US011000558B2

(12) United States Patent
Lebeer et al.

(10) Patent No.: US 11,000,558 B2
(45) Date of Patent: May 11, 2021

(54) VAGINAL PREPARATIONS FOR MAINTAINING AND/OR RESTORING HEALTHY FEMALE MICROBIOTA

(71) Applicant: Yun NV, Aartselaar (BE)

(72) Inventors: Sarah Lebeer, Antwerp (BE); Ingmar Claes, Antwerp (BE); Eline Oerlemans, Antwerp (BE); Marianne Van Den Broek, Antwerp (BE)

(73) Assignee: Yun Nv, Aartselaar (BE)

( * ) Notice: Subject to any disclaimer, the term of this patent is extended or adjusted under 35 U.S.C. 154(b) by 140 days.

(21) Appl. No.: 16/087,430

(22) PCT Filed: Mar. 21, 2017

(86) PCT No.: PCT/EP2017/056691
§ 371 (c)(1),
(2) Date: Sep. 21, 2018

(87) PCT Pub. No.: WO2017/162669
PCT Pub. Date: Sep. 28, 2017

(65) Prior Publication Data
US 2019/0054128 A1  Feb. 21, 2019

(30) Foreign Application Priority Data

Mar. 21, 2016 (BE) .................................. 2016/5201

(51) Int. Cl.
| A61K 35/747 | (2015.01) |
| A61K 9/00 | (2006.01) |
| A61P 15/02 | (2006.01) |
| A61P 31/04 | (2006.01) |
| C12R 1/225 | (2006.01) |
| C12R 1/25 | (2006.01) |

(52) U.S. Cl.
CPC .......... *A61K 35/747* (2013.01); *A61K 9/0034* (2013.01); *A61P 15/02* (2018.01); *A61P 31/04* (2018.01); *C12R 1/225* (2013.01); *C12R 1/25* (2013.01)

(58) Field of Classification Search
None
See application file for complete search history.

(56) References Cited

U.S. PATENT DOCUMENTS

| 7,541,173 B2 * | 6/2009 | Bramucci ................. C12N 1/20 435/148 |
| 9,572,845 B2 * | 2/2017 | Kim ........................ A61K 35/74 |
| 2005/0265984 A1 * | 12/2005 | Nonaka ................... A61K 35/747 424/93.45 |
| 2014/0322273 A1 * | 10/2014 | Ai ............................ C12R 1/25 424/234.1 |

FOREIGN PATENT DOCUMENTS

| KR | 20120089530 A | 8/2012 |
| KR | 20130046898 A | 5/2013 |
| WO | 9945099 A1 | 9/1999 |
| WO | 0113956 A2 | 3/2001 |
| WO | 03033681 A2 | 4/2003 |
| WO | 2007146377 A1 | 12/2007 |
| WO | 2012101550 A1 | 8/2012 |
| WO | WO-2012101500 A1 * | 8/2012 ........... A61K 35/742 |
| WO | 2015022297 A1 | 2/2015 |

OTHER PUBLICATIONS

Forbes, Claire J; et al; "Non-aqueous silicone elastomer gels as a vaginal microbicide delivery system for theHIV-1 entry inhibitor maraviroc" Journal of Controlled Release, 156, 161-169, 2011 (Year: 2011).*
International Search Report dated May 16, 2017, in reference to co-pending European Patent Application No. PCT/EP2017/056691 filed Mar. 21, 2017.
Chan, R.C et al.: "Competitive exclusion of uropathogens from human uroepithelial cells by Lactobacillus whole cells and cell wall fragments", Infection and Immunity, vol. 47, No. 1, 1985, pp. 84-89.
Chan, R.C.; Bruce, A.W.; Reid, G.: "Adherence of cervical, vaginal and distal urethral normal microbial flora to human uroepithelial cells and the inhibition of adherence of gram-negative uropathogens by competitive exclusion", The Journal of Urology, vol. 131, No. 3, 1984, pp. 596-601.
Coconnier, M.H et al.: "Antibacterial effect of the adhering human Lactobacillus acidophilus strain LB", Antimicrobial Agents and Chemotherapy, vol. 41, No. 5, 1997, pp. 1046-1052, XP002112939.
De Keersmaecker, S.C.J et al.: "Strong antimicrobial activity of Lactobacillus rhamnosus GG against *Salmonella typhimurium* is due to accumulation of lactic acid", FEMS Microbiology Letters, vol. 259, No. 1, 2006, pp. 89-96.
Doron, S.; Snydman, D.R; Gorbach, S.L.: "Lactobacillus GG: bacteriology and clinical applications", Gastroenterology Clinics of North America, vol. 34, No. 3, 2005, pp. 483-498,IX.
F. De Seta et al: "Lactobacillus plantarum P17630 for preventing Candida vaginitis recurrence: a retrospective comparative study", European Journal of Obstetrics & Gynecology and Reproductive Biology, vol. 182, Nov. 2014 (Nov. 1, 2014), IE, pp. 136-139, ISSN: 0301-2115, DOI: 10.1016/j.ejogrb.2014.09.018.
Hutt, P. et al.: "Antagonistic activity of probiotic lactobacilli and bifidobacteria against entero- and uropathogens", Journal of Applied Microbiology, vol. 100, No. 6, 2006, pp. 1324-1332.
Reid, G.; Bruce, A.W.: "Selection of lactobacillus strains for urogenital probiotic applications", The Journal of Infectious Diseases, vol. 183, 2001, pp. S77-80.
Schillinger, U.; Lucke, F.K.: "Antibacterial activity of Lactobacillus sake isolated from meat", Applied and Environmental Microbiology, vol. 55, No. 8, 1989, pp. 1901-1906.
Tomusiak Anna et al: "Efficacy and safety of a vaginal medicinal product containing three strains of probiotic bacteria: a multicenter, randomized, double-blind, and placebo-controlled trial.", Drug Design, Development and Therapy 2015, vol. 9, 2015, pp. 5345-5354, XP002763939, ISSN: 1177-8881.
Reid, G.: "The scientific basis for probiotic strains of Lactobacillus", Applied and Environmental Microbiology, vol. 65, No. 9, 1999, pp. 3763-3766.
Belgium Search Report dated May 16, 2017, in reference to co-pending European Patent Application No. PCT/EP2017/055691 filed Mar. 21, 2017.
Donders et al., Eur. J. Clin. Microbiol. Infect. Dis. DOI 10.1007/s10096-020-03868-x, Apr. 30, 2020.

* cited by examiner

*Primary Examiner* — David W Berke-Schlessel
(74) *Attorney, Agent, or Firm* — Dinsmore & Shohl LLP

(57) ABSTRACT

The present invention is directed to the direct application of beneficial or probiotic bacteria to the vaginal niche for maintenance of a healthy vaginal microbiota and to help restore an unbalanced vaginal microbiota. The application is based on the use of selected *Lactobacillus* strains as anti-pathogenic agents, in particular *L. pentosus* and/or *L. plantarum*, against common vaginal pathogens, whereby produced acids such as lactic acid are important antimicrobial factors.

13 Claims, 4 Drawing Sheets

Specification includes a Sequence Listing.

SEQUENCE LISTING

```
<160> NUMBER OF SEQ ID NOS: 4

<210> SEQ ID NO 1
<211> LENGTH: 1406
<212> TYPE: RNA
<213> ORGANISM: Lactobacillus pentosus
<220> FEATURE:
<223> OTHER INFORMATION: 16S rRNA sequence

<400> SEQUENCE: 1
cttaggcggc tggttcctaa aaggttaccc caccgacttt gggtgttaca aactctcatg      60
gtgtgacggg cggtgtgtac aaggcccggg aacgtattca ccgcggcatg ctgatccgcg     120
```

```
attactagcg attccgactt catgtaggcg agttgcagcc tacaatccga actgagaatg    180
gctttaagag attagcttac tctcgcgagt tcgcaactcg ttgtaccatc cattgtagca    240
cgtgtgtagc ccaggtcata agggcatga tgatttgacg tcatcccac cttcctccgg     300 tttgtcaccg gcagtctcac cagagtgccc aacttaatgc tggcaactga taataagggt   360
tgcgctcgtt gcgggactta acccaacatc tcacgacacg agctgacgac aaccatgcac   420
cacctgtatc catgtccccg aagggaacgt ctaatctctt agatttgcat agtatgtcaa   480
gacctggtaa ggttcttcgc gtagcttcga attaaaccac atgctccacc gcttgtgcgg   540 gccccgtca attcctttga gtttcagcct tgcggccgta ctccccaggc ggaatgctta    600
atgcgttagc tgcagcactg aagggcggaa accctccaac acttagcatt catcgtttac   660
ggtatggact accagggtat ctaatcctgt ttgctaccca tactttcgag cctcagcgtc   720
agttacagac cagacagccg ccttcgccac tggtgttctt ccatatatct acgcatttca   780
ccgctacaca tggagttcca ctgtcctctt ctgcactcaa gtttcccagt ttccgatgca   840
cttcttcggt tgagccgaag gctttcacat cagacttaaa aaaccgcctg cgctcgcttt   900
acgcccaata aatccggaca acgcttgcca cctacgtatt accgcggctg ctggcacgta   960
gttagccgtg gctttctggt taaataccgt caataccgta acagttactc tcagatatgt  1020
tcttctttaa caacagagtt ttacgagccg aaaccttct tcactcacgc ggcgttgctc   1080
catcagactt tcgtccattg tggaagattc cctactgctg cctcccgtag gagtttgggc   1140
cgtgtctcag tcccaatgtg gccgattacc ctctcaggtc ggctacgtat cattgccatg   1200
gtgagccgtt accccaccat ctagctaata cgccgcggga ccatccagaa gtgatagccg   1260
aagccatctt tcaaactcgg accatgcggt ccaagttgtt atgcggtatt agcatctgtt   1320
tccaggtgtt atccccgct tctgggcagg tttcccacgt gttactcacc agttcgccac    1380
tcactcaaat gtaaatcatg atgcaa                                        1406
```

<210> SEQ ID NO 2
<211> LENGTH: 20
<212> TYPE: DNA
<213> ORGANISM: Artificial Sequence
<220> FEATURE:
<223> OTHER INFORMATION: Primer 8F

<400> SEQUENCE: 2
agagtttgat cctggctcag                                              20

<210> SEQ ID NO 3
<211> LENGTH: 20
<212> TYPE: DNA
<213> ORGANISM: Artificial Sequence
<220> FEATURE:
<223> OTHER INFORMATION: Primer 1525R

<400> SEQUENCE: 3
aaggaggtga tccagccgca                                              20

<210> SEQ ID NO 4
<211> LENGTH: 1425
<212> TYPE: RNA
<213> ORGANISM: Lactobacillus plantarum
<220> FEATURE:
<223> OTHER INFORMATION: 16S rRNA

```
<400> SEQUENCE: 4
ggttcctaaa aggttacccc accgactttg ggtgttacaa actctcatgg tgtgacgggc      60
ggtgtgtaca aggcccggga acgtattcac cgcggcatgc tgatccgcga ttactagcga     120
ttccgacttc atgtaggcga gttgcagcct acaatccgaa ctgagaatgg ctttaagaga     180
ttagcttact ctcgcgagtt cgcaactcgt tgtaccatcc attgtagcac gtgtgtagcc     240
caggtcataa ggggcatgat gatttgacgt catccccacc ttcctccggt ttgtcaccgg     300
cagtctcacc agagtgccca acttaatgct ggcaactgat aataagggtt gcgctcgttg     360
cgggacttaa cccaacatct cacgacacga gctgacgaca accatgcacc acctgtatcc     420 atgtcccga  agggaacgtc taatctctta gatttgcata gtatgtcaag acctggtaag     480
gttcttcgcg tagcttcgaa ttaaaccaca tgctccaccg cttgtgcggg cccccgtcaa     540
ttcctttgag tttcagcctt gcggccgtac tccccaggcg gaatgcttaa tgcgttagct     600
gcagcactga agggcggaaa ccctccaaca cttagcattc atcgtttacg gtatggacta     660
ccagggtatc taatcctgtt tgctacccat actttcgagc ctcagcgtca gttacagacc     720
agacagccgc cttcgccact ggtgttcttc catatatcta cgcatttcac cgctacacat     780
ggagttccac tgtcctcttc tgcactcaag tttcccagtt tccgatgcac ttcttcggtt     840
gagccgaagg ctttcacatc agacttaaaa aaccgcctgc gctcgcttta cgcccaataa     900
atccggacaa cgcttgccac ctacgtatta ccgcggctgc tggcacgtag ttagccgtgg     960
ctttctggtt aaataccgtc aatacctgaa cagttactct cagatatgtt cttctttaac    1020
aacagagttt tacgagccga aacccttctt cactcacgcg gcgttgctcc atcagacttt    1080
cgtccattgt ggaagattcc ctactgctgc ctcccgtagg agtttgggcc gtgtctcagt    1140
cccaatgtgg ccgattaccc tctcaggtcg gctacgtatc attgccatgg tgagccgtta    1200
ccccaccatc tagctaatac gccgcgggac catccaaaag tgatagccga agccatcttt    1260
caagctcgga ccatgcggtc caagttgtta tgcggtatta gcatctgttt ccaggtgtta    1320 tccccgctt  ctgggcaggt ttcccacgtg ttactcacca gttcgccact cactcaaatg    1380
taaatcatga tgcaagcacc aatcaatacc agagttcgtt cgact                    1425
```

VAGINAL PREPARATIONS FOR MAINTAINING AND/OR RESTORING HEALTHY FEMALE MICROBIOTA

FIELD OF THE INVENTION

The present invention is directed to the direct topical application of beneficial or probiotic bacteria to the vaginal niche for maintenance of a healthy vaginal microbiota and to help restore an unbalanced vaginal microbiota. This restoration of a healthy microbiota falls under the term probiotherapy, defined as the use of beneficial micro-organisms or probiotics to restore a healthy microbiota at a site where microbial dysbiosis occurs. The application is based on the use of selected *Lactobacillus* strains as anti-pathogenic agents, in particular *L. pentosus* and/or *L. plantarum*, against common vaginal pathogens, whereby produced acids such as lactic acid are important antimicrobial factors.

BACKGROUND TO THE INVENTION

In contrast to the microbiota of the gastro-intestinal tract, the composition of the urogenital microbiota is much less complex. This microbiota develops after birth and is originating from the vaginal microbiota of the mother, the environment and migrating microbiota from the skin and lower gastro-intestinal tract. The vaginal microbiota lives in mutualism with its host and has an important role in health and disease. Although the microbial composition in healthy women can differ, it is typically dominated by one of four *Lactobacillus* species (*L. crispatus, L. iners, L. gasseri, L. jensenii*) that are commonly found in healthy individuals. However, in some cases their microbiota is dominated by several facultative anaerobic lactic acid bacteria, without a significant presence of lactobacilli. Therefore, rather than the specific bacterial species, the functional capacity of the microbiota members, among which is the production of lactic acid, plays a key role in maintaining a healthy state.

Several vaginal discomforts are a consequence of a disturbed microbial composition. Infections with *Candida albicans*, bacterial vaginosis (BV) and aerobic vaginitis (AV) are the most common encountered problems. These diseases/infections/imbalances are characterized by a lowering of the total amount of lactobacilli and overgrowth of yeast (candidose), facultative anaerobic bacteria (BV) and aerobic gram-negative bacteria (AV), respectively. Under normal circumstances, the fungus *Candida albicans* lives as commensal in the gastrointestinal and the urogenital tract. However, when the normal microbiota is disturbed, the epithelial barrier is breached or when the immune system is malfunctioning, *Candida albicans* can alter from a commensal to a pathogen. This can cause a broad spectrum of diseases including skin, mucosal and systemic infections. Over the recent years, this organism has become one of the most common causes of hospital-acquired infections. Many of these infections are caused by biofilm formation on the surfaces of medical devices, such as implants. The most important characteristic of *Candida* biofilm cells is their remarkable resistance to antifungal drugs. Often, the only solution is the mechanical removal of the implant, which is associated with increased procedural morbidity and health care expenditures. Therefore the development of new antifungal agents, in addition to now antibacterial agents, to treat these infections is of great interest.

The production of lactic acid in combination with keeping a low pH seems to give protection against aforementioned infections and dysbiotic conditions and lactic acid seems to be active against bacterial, fungal and even viral pathogens. It is for this reason that lactobacilli are considered to be important in the homeostasis of the dynamical vaginal ecosystem. Potential health promoting mechanisms of lactobacilli are i) to preserve a low vaginal pH (<4.5), mainly by production of lactic acid; ii) production of antimicrobial compounds and competitive exclusion of pathogens; iii) modulation of immune response and iv) strengthening of the epithelial barrier.

Hence, it was an object of the present invention to provide a solution for subjects suffering from vaginal discomforts due to an aberrant microbial balance in the vagina. Thereto, it was found that the topical vaginal use of *L. pentosus* species is very effective in restoring and/or maintaining a healthy microbiota in the vagina, and is thus very suitable in relieving vaginal discomforts in subjects in need thereof.

Oral formulations comprising *Lactobacillus* strains have been used before in the treatment of vaginal disorders or for restoring and/or maintaining a healthy microbiota in the vagina. However, oral administration versus direct topical administration are different administration routes and each have a completely different underlying mechanism. In oral administration, in particular a beneficial effect on the general health via immuno-stimulation is intended, whereas by direct vaginal administration, competition with 'unwanted' microorganisms occur.

Topical vaginal administration of compositions comprising live *Lactobacillus* strains, were found to be useful in the treatment of vaginal infections, such as for example mentioned in WO2012101550, WO15022297, WO03033681, WO0113956, WO20040350726. However, these do not address the use thereof in the restoration and/or maintenance of a healthy vaginal microbiota.

A very recent publication by Tomusiak et al. indicates the relevance of the current invention (Tomusiak et al., 2015). In particular, Tomusiak et al. found that the vaginal administration of *Lactobacillus* strains sustainably restores the healthy vaginal microbiota. Further to the findings of Tomusiak that were based on *L. fermentum, L. plantarum* and *L. gasseri* species, we have found that *L. pentosus* is particularly suitable in the context of the present invention. Furthermore, Tomusiak used an intravaginal capsule to formulate the *Lactobacillus* species, whereas we found that the formulation in a non-solid composition is much more effective, due to a better spreading capacity along the vaginal epithelial cells.

SUMMARY OF THE INVENTION

In a first aspect, the present invention provides a topical vaginal composition comprising one or more live *Lactobacillus* species; wherein at least one of said *Lactobacillus* species is *L. pentosus*; more in particular a *L. pentosus* strain having at least 97% sequence similarity with SEQ ID No 1 in its 16S rRNA gene.

In a further aspect, the present invention provides a live *Lactobacillus* species for use in restoring and/or maintaining a healthy female microbiota, by topical vaginal route, said *Lactobacillus* species being *L. pentosus*; more in particular a *L. pentosus* strain having at least 97% sequence similarity with SEQ ID No 1 in its 16S rRNA gene.

In yet a further aspect, the present invention provides the use of one or more live *Lactobacillus* species, in the preparation of a topical vaginal composition for restoring and/or maintaining a healthy female microbiota; wherein at least one of said *Lactobacillus* species is *L. pentosus*; more in particular a *L. pentosus* strain having at least 97% sequence similarity with SEQ ID No 1 in its 16S rRNA gene.

The present invention also provides a method for restoring and/or maintaining a healthy female microbiota; comprising at least one step of administering by topical vaginal route, to an individual, an effective amount of one or more live *Lactobacillus* species; wherein at least one of said *Lactobacillus* species is *L. pentosus*; more in particular a *L. pentosus* strain having at least 97% sequence similarity with SEQ ID No 1 in its 16S rRNA gene.

In yet another aspect, the present invention provides a composition comprising one or more live *Lactobacillus* species for use in restoring and/or maintaining a healthy female microbiota, by topical vaginal route, said *Lactobacillus* species being selected from the list comprising *L. pentosus* and *L. plantarum*, more in particular *L. pentosus*; even more in particular a *L. pentosus* strain having at least 97% sequence similarity with SEQ ID No 1 in its 16S rRNA gene and a *L. plantarum* strain having at least 97% sequence similarity with SEQ ID No 4 in its 16S rRNA gene.

The present invention further provides a *Lactobacillus* strain selected from the list comprising *L. pentosus* YUN-V1.0 deposited under accession number LMG P-29455 (deposited at BCCM on Mar. 9 2016); and *L. plantarum* YUN-V2.0 deposited under accession number LMG P-29456 (deposited at BCCM on Mar. 9 2016).

In a particular aspect, the present invention provides a composition comprising one or more *Lactobacillus* strains as defined herein above.

In a particular embodiment, the composition of the present invention is a topical vaginal composition, more in particular in the form of a gel, cream, foam, lotion or ointment.

In another particular embodiment, the present invention provides the *Lactobacillus* strain as defined herein above or the compositions as defined herein above; for use in restoring and/or maintaining a healthy female microbiota, by topical vaginal route.

In a particular aspect, the present invention provides a topical vaginal use of one or more live *Lactobacillus* species in probiotherapy; wherein said *Lactobacillus* species are selected from the list comprising *L. pentosus* and *L. plantarum*; more in particular, said said probiotherapy consists of restoring and/or maintaining a healthy female microbiota in a subject in need thereof.

In another particular embodiment, said *Lactobacillus* species in the (topical vaginal) uses, methods and compositions as disclosed herein, is a *Lactobacillus* strain selected from the list comprising *L. pentosus* YUN-V1.0 deposited under accession number LMG P-29455 (deposited at BCCM on Mar. 9 2016); and *L. plantarum* YUN-V2.0 deposited under accession number LMG P-29456 (deposited at BCCM on Mar. 9 2016).

BRIEF DESCRIPTION OF THE DRAWINGS

With specific reference now to the figures, it is stressed that the particulars shown are by way of example and for purposes of illustrative discussion of the different embodiments of the present invention only. They are presented in the cause of providing what is believed to be the most useful and readily description of the principles and conceptual aspects of the invention. In this regard no attempt is made to show structural details of the invention in more detail than is necessary for a fundamental understanding of the invention. The description taken with the drawings making apparent to those skilled in the art how the several forms of the invention may be embodied in practice.

B) Detection of the exogeneously added *Lactobacillus* strains at visits 2 and 3 when the probiotic cream was used.

Figure 5:
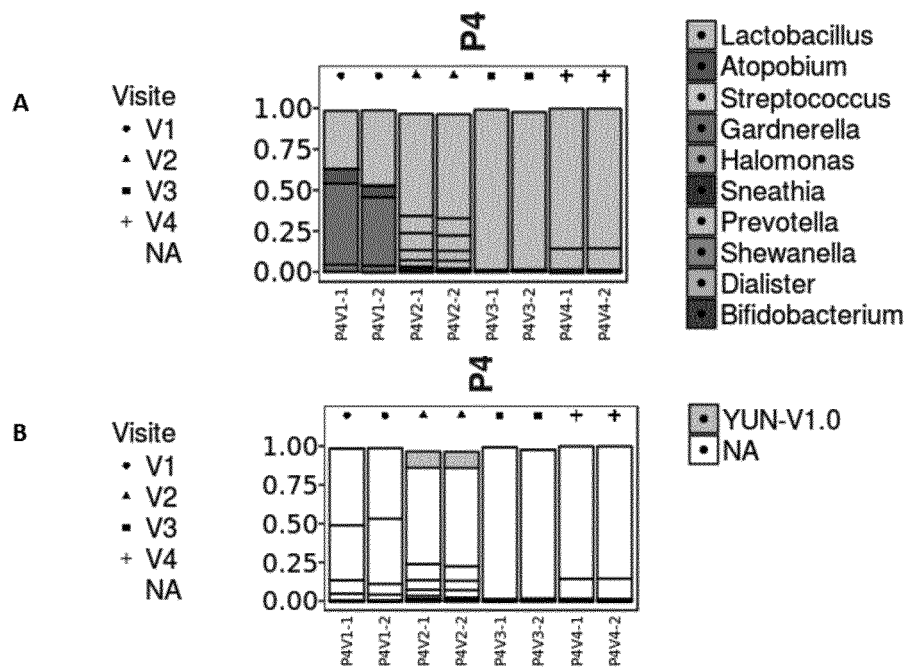

FIG. 5: A) The bacterial microbiome profile of a patient with vaginal candidose enrolled in the proof-of-concept clinical trial.

B) Detection of the exogeneously added *Lactobacillus* strains at visits 2 and 3 when the probiotic cream was used.

DETAILED DESCRIPTION OF THE INVENTION

The present invention is based on the discovery of specific *Lactobacillus* strains that can compete with the growth of *Candida albicans* and bacteria that are linked with bacterial vaginosis and aerobic vaginitis. These selected strains are herein generally termed "YUN" strains and are capable of competing with vaginal pathogens and thereby restore a healthy vaginal microbiota. This restoration of a healthy microbiota falls under the term probiotherapy, defined as the use of beneficial micro-organisms or probiotics to restore a healthy microbiota at a site where microbial dysbiosis occurs.

Hence, in a first aspect, the present invention provides a topical vaginal composition comprising one or more live *Lactobacillus* species; wherein at least one of said *Lactobacillus* species is *L. pentosus*; more in particular a *L. pentosus* strain having at least 97% sequence similarity with SEQ ID No 1 in its 16S rRNA gene.

Said composition according to the present invention may comprise further *Lactobacillus* species such as for example selected from the non-limiting list comprising *L. plantarum, L. gasseri, L. crispatus, L. acidophilus, L. jensenii, L. fermentum, L. rhamnosus*.

In the context of the present invention, the term "topical" is meant to be the local delivery at a specified location of the body, in particular the application to a particular place on or in the body. In particular, it includes the application to mucous membranes via non-solid formulations such as creams, foams, gels, lotions or ointments. The term "topical" is not meant to include the delivery in the form of solid preparations such as capsules, tablets, . . . .

Hence, the term "topical vaginal" is meant to include the local delivery using non-solid formulations directly in the vaginal tract of the body. Preferably, the compositions according to the present invention are applied over a large area of the mucous membranes of the vagina in order to be most effective.

In the context of the present invention the term "live *Lactobacillus* species" is meant to be viable *Lactobacillus* species, and is not meant to be fragments, culture supernatants, or killed forms thereof.

In a further aspect, the present invention provides a live *Lactobacillus* species for use in probiotherapy, by topical vaginal route, said *Lactobacillus* species being *L. pentosus*; more in particular a *L. pentosus* strain having at least 97% sequence similarity with SEQ ID No 1 in its 16S rRNA gene. As already defined herein above, said probiotherapy is meant to be the restoration and/or maintainance of a healthy female microbiota in a subject in need thereof.

Subjects that may benefit from such probiotherapy are for example female patients with a disturbed vaginal microbiota possibly due to a vaginal yeast infection, bacterial vaginosis, aerobic vaginitis and/or any dysbiosis caused by overgrowth of other micro-organisms than lactobacilli.

Hence, in a further aspect, the present invention provides the use of one or more live *Lactobacillus* species, in the preparation of a topical vaginal composition for restoring and/or maintaining a healthy female microbiota; wherein at least one of said *Lactobacillus* species is *L. pentosus*; more in particular a *L. pentosus* strain having at least 97% sequence similarity with SEQ ID No 1 in its 16S rRNA gene.

The present invention also provides a method for restoring and/or maintaining a healthy female microbiota; comprising at least one step of administering by topical vaginal route, to an individual, an effective amount of one or more live *Lactobacillus* species; wherein at least one of said *Lactobacillus* species is *L. pentosus*; more in particular a *L. pentosus* strain having at least 97% sequence similarity with SEQ ID No 1 in its 16S rRNA gene.

In yet another aspect, the present invention provides a composition comprising one or more live *Lactobacillus* species for use in restoring and/or maintaining a healthy female microbiota, by topical vaginal route, said *Lactobacillus* species being selected from the list comprising *L. pentosus* and *L. plantarum*, more in particular *L. pentosus*; even more in particular a *L. pentosus* strain having at least 97% sequence similarity with SEQ ID N° 1 in its 16S rRNA gene and a *L. plantarum* strain having at least 97% sequence similarity with SEQ ID No 4 in its 16S rRNA gene.

The present invention further provides a *Lactobacillus* strain selected from the list comprising *L. pentosus* YUN-V1.0 deposited under accession number LMG P-29455 (deposited at BCCM on Mar. 9 2016); and *L. plantarum* YUN-V2.0 deposited under accession number LMG P-29456 (deposited at BCCM on Mar. 9 2016).

The microbiological deposits mentioned herein, have been made with the BCCM/LMG Bacteria collection ("Belgian co-ordinated collections of micro-organism") with correspondence address: Laboratorium voor Microbiologie, Universiteit Gent, K. L. Ledeganckstraat 35-9000 Gent, Belgium

*Lactobacillus pentosus* YUN-V1.0 is a single colony isolate obtained in our lab after subculturing of a strain that was originally a vaginal isolate of healthy woman. The 16S rRNA gene sequence (SEQ ID No 1) for strain *L. pentosus* YUN-V1.0 was determined by PCR using primers 8F (5'-AGAGTTTGATCCTGGCTCAG-3'-SEQ ID No 2) and 1525R (5'-AAGGAGGTGATCCAGCCGCA-3'-SEQ ID No 3).

YUN-V2.0 and YUN-V3.0 are single colony isolates obtained in our lab after subculturing of *Lactobacillus plantarum* strains that were originally isolated from human saliva and a maize silage respectively. The 16S rRNA gene sequence (SEQ ID No 4) for strain *L. plantarum* YUN-V2.0 was determined by PCR using primers 8F (5'-AGAGTTT-GATCCTGGCTCAG-3'-SEQ ID No 2) and 1525R (5'-AAGGAGGTGATCCAGCCGCA-3'-SEQ ID No 3).

These particular "YUN" strains can either be used as such, or are preferably formulated in a composition comprising such strains. Said compositions are topical vaginal compositions more in particular in the form of non-solid formulations such as creams, foams, gels, lotions or ointments.

In particular, the present invention provides the above defined "YUN" strains for use in probiotherapy, i.e. for restoring and/or maintaining a healthy female microbiota, by topical vaginal route.

In yet a further aspect, the present invention provides a topical vaginal use of one or more live *Lactobacillus* species in probiotherapy; wherein said *Lactobacillus* species are selected from the list comprising *L. pentosus* and *L. plantarum*; more in particular, said probiotherapy consists of restoring and/or maintaining a healthy female microbiota in a subject in need thereof.

In a specific embodiment, the *Lactobacillus* species in the (topical vaginal) uses, methods and compositions as disclosed herein, is a *Lactobacillus* strain selected from the list comprising *L. pentosus* YUN-V1.0 deposited under accession number LMG P-29455 (deposited at BCCM on Mar. 9 2016); and *L. plantarum* YUN-V2.0 deposited under accession number LMG P-29456 (deposited at BCCM on Mar. 9 2016).

EXAMPLES

Materials and Methods
Bacterial Strains and Growth Conditions

*Lactobacillus* strains (Table 1) were grown at 37° C. in de Man, Rogosa and Sharpe (MRS) medium (Carl Roth). All bacteria were grown in non-shaking conditions and inoculated from glycerol stocks (−80° C.). Solid media contained 1.5% (w/v) agar.

TABLE 1

Bacterial strains used in this research

| Species | # Strain | Relevant genotype or description | Reference and/or Source |
| --- | --- | --- | --- |
| LACTOBACILLI | | | |
| *Lactobacillus casei* | 1 ATCC334 | Single colony isolate obtained in our lab from a stock culture of ATCC334 | ATCC |
| *Lactobacillus casei* | 2 DN-114001 | Single colony isolate obtained in our lab from a commercially available fermented drink (Actimel ®) containing *L. casei* DN-114001, confirmed by sequencing | Commercial probiotic product |

TABLE 1-continued

Bacterial strains used in this research

| Species | # | Strain | Relevant genotype or description | Reference and/or Source |
|---|---|---|---|---|
| Lactobacillus casei | 3 | Shirota | Single colony isolate obtained in our lab from a commercially available fermented drink containing L. casei Shirota (Yakult ®), confirmed by sequencing | Commercial probiotic product |
| Lactobacillus pentosus | 4 | YUN-V1.0 | Single colony isolate | |
| Lactobacillus plantarum | 5 | LMG1284 | Single colony isolate from L. plantarum ATCC8014 or LMG1284 | ATCC |
| Lactobacillus reuteri | 6 | RC-14 | Single colony isolate obtained in our lab from a commercially available probiotic supplement containing L. reuteri RC-14, confirmed by sequencing | Commercial probiotic product |
| Lactobacillus rhamnosus | 7 | GG | Wild type strain, isolated from human faeces | (Doron et al. 2005) |
| Lactobacillus rhamnosus | 12 | GR-1 | Single colony isolate obtained in our lab from a commercially available probiotic supplement containing L. rhamnosus GR-1 | (Chan et al. 1984, 1985; Reid 1999; Reid and Bruce 2001), ATCC |
| Lactobacillus helveticus | 14 | AMB-2 | single colony isolate | Commercial probiotic product |
| Lactobacillus plantarum | 15 | YUN-V2.0 | Single colony isolate | |
| Lactobacillus plantarum | 16 | YUN-V3.0 | Single colony isolate | |
| Lactobacillus paracasei | 17 | LMG12586 | Single colony isolate obtained in our lab from a stock culture of LMG12586 | BCCM/LMG |
| Lactobacillus plantarum | 22 | / | Single colony isolate | |
| Lactobacillus pentosus | 25 | LMG8041 | Single colony isolate | BCCM/LMG |
| PATHOGENS | | | | |
| Candida albicans | / | / | Clinical isolate | |

Preparation of Spent Culture Supernatant (SCS) of Selected Strains

To obtain spent culture supernatant (SCS) containing the secreted active antimicrobial products, growth medium specific for each species was inoculated from a preculture and incubated for 24 h. SCS was obtained by centrifugation for 30 min. at 6797 g (8000 rpm) at 4° C. Afterwards, the SCS was filter sterilized (0.20 µm cellulose acetate, VWR).

Antimicrobial Activity Assays for Co-Cultures of Live Lactobacilli Against Candida, BV and AV Indicator Strains The antimicrobial activity of the selected bacteria was explored by standard antimicrobial tests with some minor modifications. For the streak inoculation assay, lactobacilli were streak inoculated from a colony on a starter plate (MRS) on a test plate (medium of pathogen) and incubated at 37° C. for 54 h. Then, the pathogens were streak inoculated from a colony on a starter plate on the test plates in 3 repetitions. The plates were incubated at 37° C. for 24 h and the inhibition zone was measured as described previously (Hütt et al. 2006). In addition, the antimicrobial activity of the selected bacteria were explored by spot assay (Schillinger and Lücke 1989). Briefly, 1-3 µL of each culture was spotted on an agar plate. These plates were incubated for 24 h up to 72 h depending on the strain. Next, an overnight culture of the pathogen was diluted into 7 mL of soft agar of the medium of the pathogen and poured over the plates with the spots of the selected strains. The plates were incubated overnight at 37° C., after which the inhibition zones were measured. A spot of miconazole and/or 0.1% hexetidine was added to the spot plate as positive control before the soft agar was poured.

Radial Diffusion Test of SCS of Lactobacilli

In addition, the antimicrobial activity of spent culture supernatant (SCS) was investigated with a protocol as previously described for the competition assays between lactobacilli and gastro-intestinal pathogens (Coconnier et al. 1997). Miconazole was used as a positive control. Sterile growth medium was used as a negative control.

Time Course Analysis of the Antimicrobial Activity of SCS of the Selected Strains Against Candida, BV and AV Indicator Strains The time course analysis was performed as described previously (De Keersmaecker et al. 2006) with minor modifications. Briefly, an overnight culture of C. albicans, Gardnerella vaginalis (BV) or Streptococcus agalactiae (AV) was added to the wells of a microplate filled with 50-80% the proper medium supplemented with 50-5% SCS of lactobacilli. MRS at pH 4,3 and miconazole (0.02 µg/ml final concentration) were used as a negative and a positive control, respectively. Bacteria were grown and the optical density (OD) was measured at 590 nm each 30 min during 3 days using a Synergy HTX multi-mode reader (Biotek).

Each test was measured at least in triplicate and the average OD was calculated. The antimicrobial activity was expressed as the relative optical density reached after 24 h (stationary phase) compared to the negative controls.

Safety Assessment of Probiotherapy Using In Vitro Cell Cultures

As a first indicator of safety, the ability of the *Lactobacillus* strains to elicit a pro-inflammatory response in the form of an upregulation of interleukin 8 in the VK2/E6E7 cell line, an immortalized vaginal epithelium cell line, was tested. VK2/E6E7 cells were grown to a confluent monolayer and exposed to 1.5. $10^7$CFU's or miconazole (0.2 µg/ml final concentration) for approximately 90 minutes, after which RNA was extracted. RT-qPCR was used to determine relative expression levels of IL8, compared to those of reference genes actinβ (ACTb) and glyceraldehyde 3-phosphate dehydrogenase (GAPDH).

Proof-of-Concept Human Clinical Trial in Patients with Vaginal Candidose

A proof-of-concept clinical trial was performed on 20 patients with vaginal candidose. Patients were between 18-45 years and had severe inflammation (vaginitis). The aim of this proof-of-concept trial was to assess the impact of a vaginal silicon-based gel containing 10% probiotic powder (fit-for-purpose vaginal anhydrous system: containing +−10-11 colony forming units (CFU) of *L. pentosus* YUN-V1.0 and +−10-11 CFU of *L. plantarum* YUN-V2.0 per application of 2-2.5 ml of an anhydrous system) on the vaginal microbiota and on the *Candida* infection. The formulation was produced by blending the bacterial powder under vacuum in the silicon-based gel and filled in aluminum-coated tubes of 30 ml. Patients were asked to daily apply the cream intravaginally using an applicator for 10 days. The patients were seen by a gynaecologist at day 0 (before the therapy), day 1, day 5 and day 10. A vaginal washing sample was taken at each visit. Bacterial DNA was isolated from these samples by the commercial MoBio Powersoil kit (cfr. Human Microbiome Project). Isolated DNA was analysed via 16S rRNA amplicon sequencing with MiSeq Illumina and a bio-informatical analysis was performed. The same washing samples were also used to determine *Candida albicans* counts by selective agar plating (Sabouraud Dextrose agar or similar). Moreover, a clinical scoring was performed at each visit.

Antibiotic Susceptibility

Antibiotic sensitivity was evaluated using the Kirby-Bauer disc diffusion test. In short, antibiotics were spotted on paper discs and the bacterial inhibition zone was measured on agar plates. The antibiotics tested were erythromycin, normocin, tetracyclin, ampicillin and clindamycin at relevant concentrations.

Results

Growth Characteristics and Lactate Production

Figure 1:
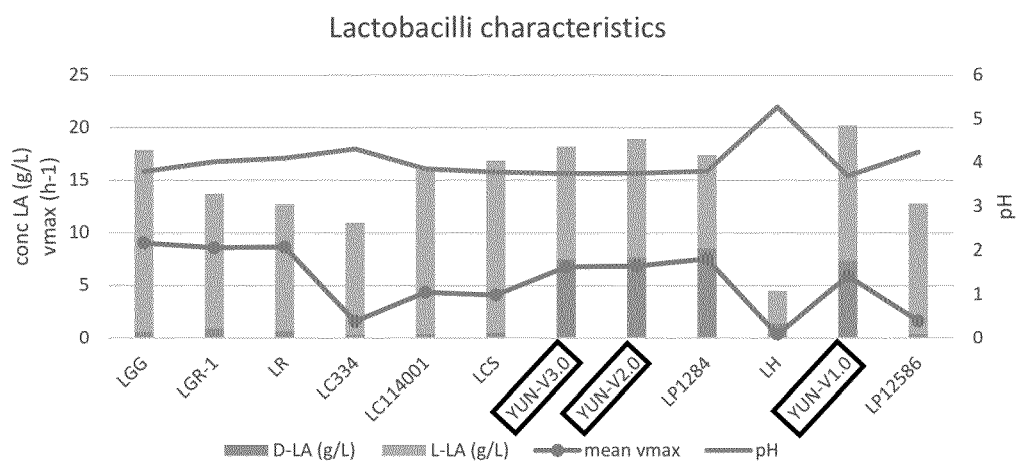
FIG. 1: Characteristics of lactobacilli in reference to growth, production of D- and L-lactic acid (LA) and lowering of the pH of the medium.

Possible beneficial or probiotic strains were characterized in terms of growth characteristics, lactate production (based on D- and L-lactic acid production) and ability of lowering of the pH of the medium. These characteristics are expected to be important in maintenance and/or restoring the healthy vaginal microbiota. These data show that *Lactobacillus pentosus* YUN-V1.0 and *L. plantarum* YUN-V2.0 and YUN-V3.0 produce the highest amount of lactic acid, in particular due to a significant increase in D-Lactic Acid production (see FIG. 1).

Antipathogenic Assays

In a next phase, the beneficial or probiotic bacteria were screened for their antipathogenic effect against *Candida albicans*. The results of a radial diffusion test are shown in table 2. Spent culture supernatant from *L. pentosus* YUN-V1.0 was demonstrated to be superior in inhibiting *Candida albicans* growth. *L. plantarum* YUN-V2.0 and YUN-V3.0 showed inhibition to a smaller extent but still better or similar than most of the other *Lactobacillus* strains.

TABLE 2

Radial diffusion test using spent culture supernatant (SCS) from lactobacilli to inhibit growth of *Candida albicans*

| Number | Strain | Candida inhibition |
|---|---|---|
| 1 | *Lactobacillus casei* ATCC334 | − |
| 2 | *Lactobacillus casei* Immunitas | + |
| 3 | *Lactobacillus casei* Shirota | + |
| 4 | *Lactobacillus pentosus* YUN-V1.0 | ++ |
| 5 | *Lactobacillus plantarum* LMG1284 or ATCC8014 | + |
| 6 | *Lactobacillus reuteri* RC-14 | − |
| 7 | *Lactobacillus rhamnosus* GG (=LGG) | + |
| 12 | *Lactobacillus rhamnosus* GR-1 | + |
| 14 | *Lactobacillus helveticus* | − |
| 15 | *Lactobacillus plantarum* YUN-V2.0 | + |
| 16 | *Lactobacillus plantarum* YUN-V3.0 | + |
| 17 | *Lactobacillus paracasei* subsp. *paracasei* | − |

A spot-based antipathogenic assay was also performed to investigate the anti-pathogenic activity of the selected live *Lactobacillus* species against *Candida albicans*. The selected strains all inhibited growth of *Candida* to some extent but the most effective strains were *L. plantarum* YUN-V2.0 and *L. plantarum* YUN-V3.0 (see table 3).

TABLE 3

Spot assay of different lactobacilli strains using an overlay of *Candida albicans*.

| Number | Strain | Candida inhibition |
|---|---|---|
| 4 | *Lactobacillus pentosus* YUN-V1.0 | + |
| 5 | *Lactobacillus plantarum* LMG1284 of ATCC8014 | + |
| 7 | *Lactobacillus rhamnosus* GG (=LGG) | + |
| 12 | *Lactobacillus rhamnosus* GR-1 | + |
| 15 | *Lactobacillus plantarum* YUN-V2.0 | ++ |
| 16 | *Lactobacillus plantarum* YUN-V3.0 | ++ |
| 22 | *Lactobacillus plantarum* | + |
| 25 | *Lactobacillus pentosus* LMG 8041 | + |

Figure 2A:
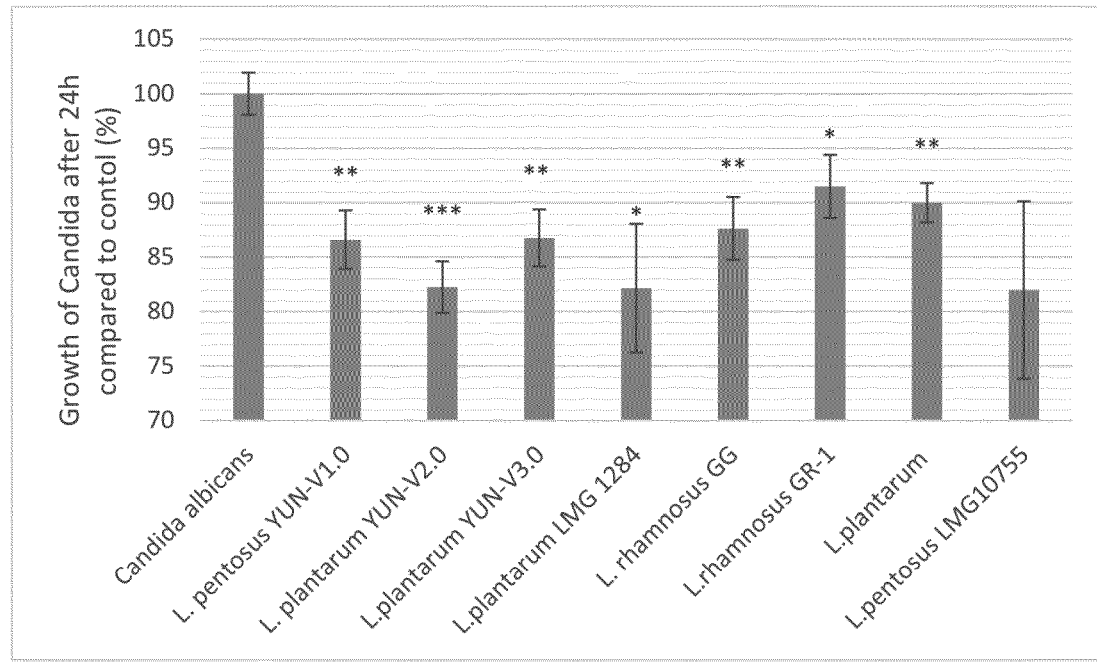
FIG. 2: Proportional growth of *Candida* after 24 h in YPD medium supplemented with SCS of lactobacilli compared to negative control (MRS at pH4), as measured by spectrophotometry (OD 600).
Figure 2B:
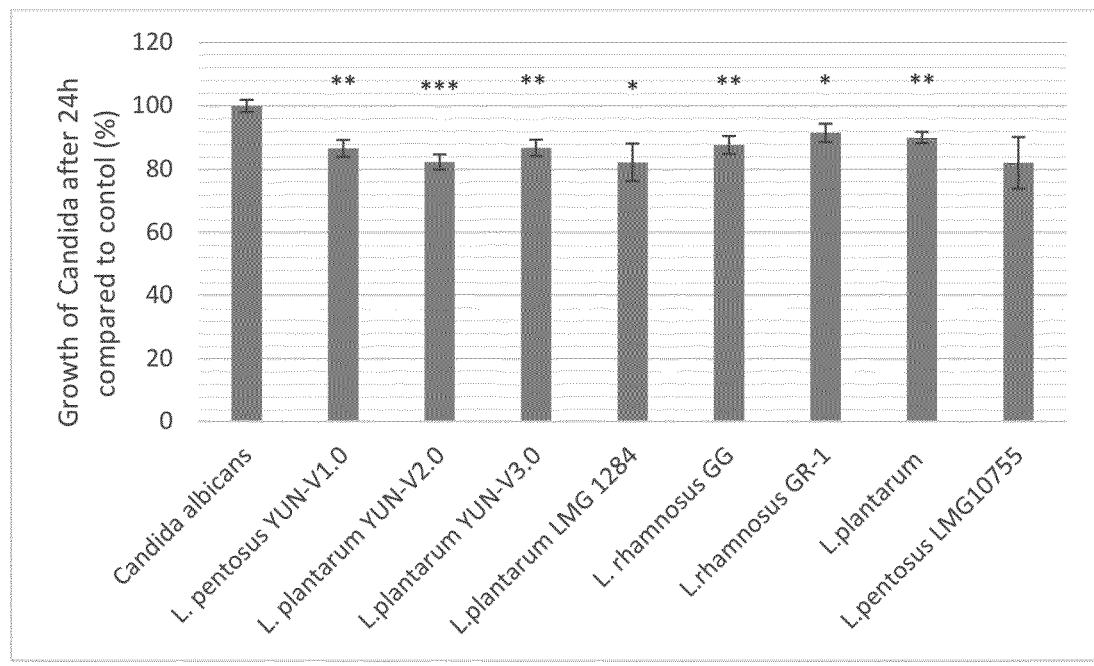
Figure 2C:
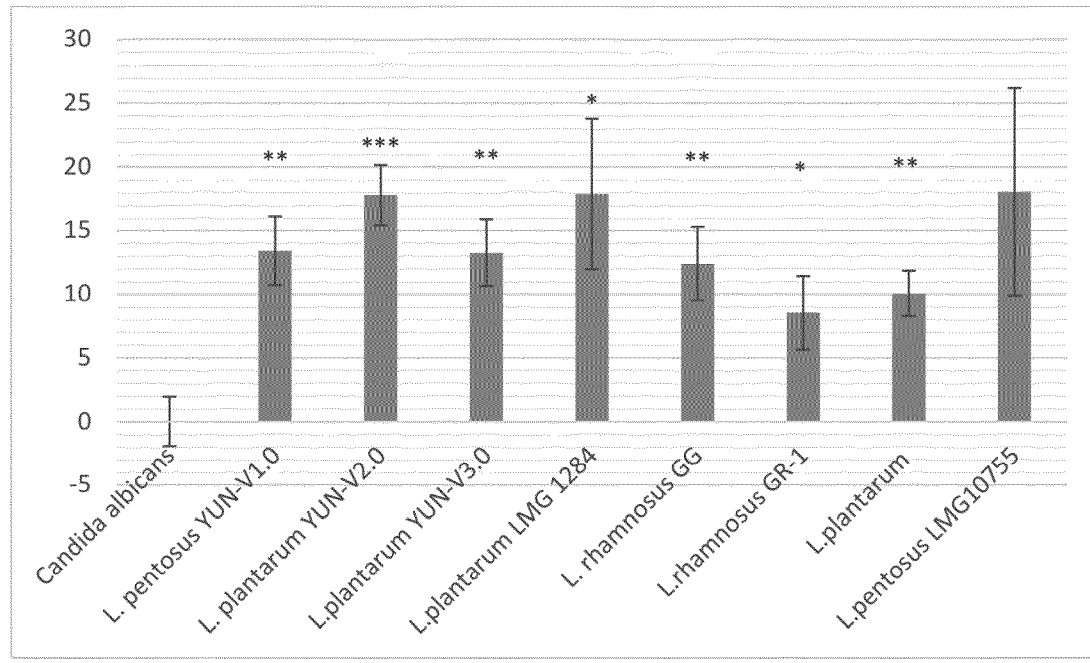

Thirdly, time course experiments were performed analyzing the antimicrobial activity of SCSs of the selected strains against *Candida*. Again, SCSs of all tested strains inhibited the growth of *Candida* to some extent, while most effective strains were *L. plantarum* YUN-V1.0, *L. plantarum* YUN-V2.0 and *L. plantarum* YUN-V3.0 (see FIG. 2).

Safety Assessment of Probiotherapy Using In Vitro Cell Cultures

Figure 3:
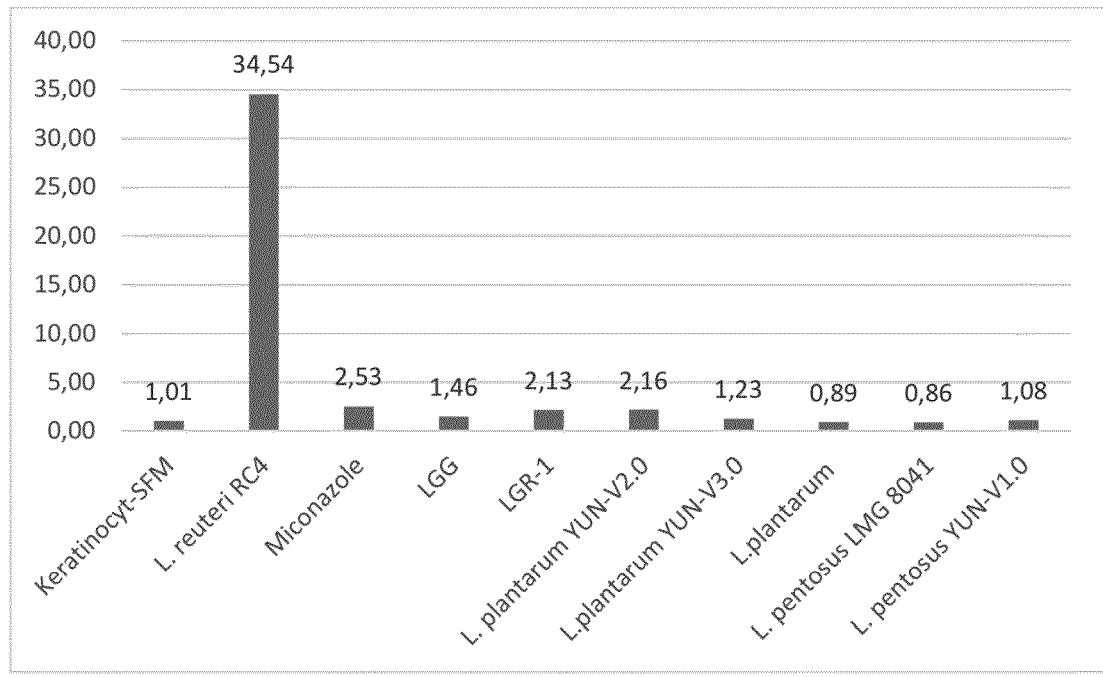
FIG. 3: Change in expression levels of interleukin 8 in VK2/E6E7 cells following exposure to lactobacilli.

As an indicator of safety, the ability of the strains to induce the pro-inflammatory chemokine interleukin 8, was analyzed. Some strains showed a relatively small increase in expression, but as desired none of the tested strains elicited a strong interleukin 8 response. However, a clear IL-8 upregulation was observed for *L. reuteri* RC-14 (FIG. 3). It is important to note here that the miconazole data could be influenced by an effect of the miconazole treatment on the cell viability.

It was observed by microscopy that a larger number of cells had died during the treatment, compared to the negative control.

Case Studies from Proof-of-Concept Human Clinical Trial in Patients with Vaginal Candidose The vaginal microbiome of patients with acute vaginal candidose in a proof-of-concept clinical trial was analyzed at different time points. In general, two different groups could be observed at the start of the trial: i) one group of patients where the endogenous vaginal lactobacilli are still present but where these lactobacilli were not able to protect against the yeast infection and ii) a second group of patients where the bacterial microbiome is disturbed and a loss of lactobacilli is observed. In these patients, other non-lactobacilli, e.g. *Atopobium* spp. and *Gardnerella* spp. show up in addition to the yeast infection.

In what follows, two case studies are highlighted of patients which were enrolled in the study and were cured by using the vaginal probiotic gel containing *L. pentosus* YUN-V1.0 and *L. plantarum* YUN-V2.0.

Figure 4:
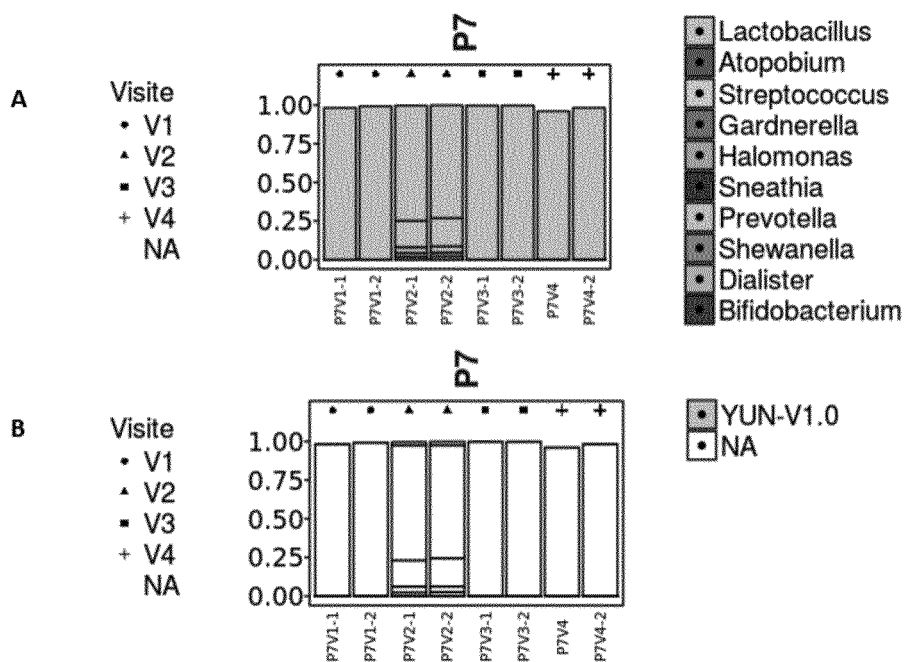
FIG. 4: A) The bacterial microbiome profile of a patient with vaginal candidose enrolled in the proof-of-concept clinical trial.

Case Study 1:

In FIG. 4A at the first visit the patient (P7) was diagnosed as having acute candidose. The accompanying bacterial microbiome profile was dominated by *lactobacillus* proving that the endogenous present lactobacilli were not able to prevent the yeast infection. However, after use of the probiotic vaginal cream with the specifically selected lactobacilli strains *L. pentosus* YUN-V1.0 and *L. plantarum* YUN-V2.0, the patient was symptom- and *Candida*-free at visit 3 and remained symptom-free at visit 4, one week after stopping the intravaginal probiotic treatment. At visit 2, after 2 weeks of intravaginal use of the YUN probiotic cream, as can be seen in FIG. 4B, the OTU (operational taxonomical unit) with 100% identity with strain *L. pentosus* YUN-V1.0 is highlighted and can be found in samples at visit 2. This patient was cured using the vaginal probiotic cream.

Case Study 2:

In FIG. 5A, at the first visit, this patient was diagnosed as having acute candidose. Based on the microbiome profile, it could be observed that this patient was not dominated by lactobacilli as typically seen in a healthy vaginal flora but bacteria often linked to bacterial vaginosis, i.e. *Gardnerella* spp. and *Atopium* spp. were observed. Interestingly, one specific operational taxonomical unit (OTU) of lactobacilli was still present at visit 1 and identified as '*Lactobacillus*' at genus level and which based on the sequence could be either one of the following species '*acidophilus/casei/crispatus/gallinarum/helveticus/kitasatonis*'. This implies that this OTU could be present alongside the *Candida* spp. but was not strong enough to prevent the candidose. At visit 2, after 2 weeks of intravaginal use of the YUN probiotic cream, as shown in FIG. 5B, the OTU with 100% identity with strain *L. pentosus* YUN-V1.0 is highlighted and can be found in the samples. After these two weeks, this patient was symptom-free and the vaginal microbiome was completely dominated by lactobacilli. The YUN vaginal probiotic cream helped in rebalancing towards a healthy vaginal microflora dominated by lactobacilli.

Antibiotic Susceptibility

The selected bacteria were also tested for their antibiotic susceptibility as to prevent spreading of antibiotic resistance genes. All lactobacilli were susceptible to erythromycin, normocin, tetracyclin, ampicillin and clindamycin, except for *L. plantarum* 5057, which was susceptible to tetracyclin. For this reason, strain *L. plantarum* 5057 was found not to be suitable to use as a strain for probiotherapy.

REFERENCES

Chan, R. C. et al., 1985. Competitive exclusion of uropathogens from human uroepithelial cells by *Lactobacillus* whole cells and cell wall fragments. Infection and immunity, 47(1), pp. 84-9.

Chan, R. C., Bruce, A. W. & Reid, G., 1984. Adherence of cervical, vaginal and distal urethral normal microbial flora to human uroepithelial cells and the inhibition of adherence of gram-negative uropathogens by competitive exclusion. The Journal of urology, 131(3), pp. 596-601.

Coconnier, M. H. et al., 1997. Antibacterial effect of the adhering human *Lactobacillus acidophilus* strain LB. Antimicrobial agents and chemotherapy, 41(5), pp. 1046-52.

Doron, S., Snydman, D. R. & Gorbach, S. L., 2005. *Lactobacillus* GG: bacteriology and clinical applications. Gastroenterology clinics of North America, 34(3), pp. 483-98, ix.

Hütt, P. et al., 2006. Antagonistic activity of probiotic lactobacilli and bifidobacteria against entero- and uropathogens. Journal of applied microbiology, 100(6), pp. 1324-32.

De Keersmaecker, S. C. J. et al., 2006. Strong antimicrobial activity of *Lactobacillus rhamnosus* GG against *Salmonella typhimurium* is due to accumulation of lactic acid. FEMS microbiology letters, 259(1), pp. 89-96.

Reid, G., 1999. The scientific basis for probiotic strains of *Lactobacillus*. Applied and environmental microbiology, 65(9), pp. 3763-6.

Reid, G. & Bruce, A. W., 2001. Selection of *lactobacillus* strains for urogenital probiotic applications. The Journal of infectious diseases, 183 Suppl, pp. S77-80.

Schillinger, U. & Lücke, F. K., 1989. Antibacterial activity of *Lactobacillus* sake isolated from meat. Applied and environmental microbiology, 55(8), pp. 1901-6.

Tomusiak, A. et al., 2015. Efficacy and safety of a vaginal medicinal product containing three strains of probiotic bacteria: a multicenter, randomized, double-blind, and placebo-controlled trial. Drug design, development and therapy, 9, pp. 5345-54.

The invention claimed is:

1. A method for restoring or maintaining a healthy female microbiota the method comprising: administering by a topical vaginal route, an effective amount of a *Lactobacillus pentosus* strain having at least 97% sequence similarity with SEQ ID NO: 1 in its 16S rRNA gene and a *Lactobacillus plantarum* strain having at least 97% sequence similarity with SEQ ID NO: 4 in its 16S rRNA gene.

2. The method of claim 1, wherein the *L. pentosus* strain is *L. pentosus* YUN-V1.0 deposited under accession number LMG P-29455.

3. The method of claim 1, wherein the *L. plantarum* strain is *L. plantarum* YUN V2.0 deposited under accession number LMG P-29456.

4. A composition comprising a silicon-based gel and a *Lactobacillus pentosus* strain having at least 97% sequence similarity with SEQ ID NO: 1 in its 16S rRNA gene and a *Lactobacillus plantarum* strain having at least 97% sequence similarity with SEQ ID NO: 4 in its 16S rRNA gene.

5. The composition of claim 4, wherein the *L. pentosus* strain is *L. pentosus* YUN-V1.0 deposited under accession number LMG P-29455.

6. The composition of claim 4, wherein the *L. plantarum* strain is *L. plantarum* YUN V2.0 deposited under accession number LMG P-29456.

7. The composition of claim 4, wherein the composition is a topical vaginal composition.

8. The composition of claim 4, wherein the composition is a topical vaginal composition in the form of a gel, a cream, an ovule, a suppository, a foam, a lotion, or an ointment.

9. A method of probiotherapy, the method comprising: administering an effective amount of live *Lactobacillus* species to a subject in need of the probiotherapy by a topical vaginal route, wherein said *Lactobacillus* species are a *L. pentosus* strain having at least 97% sequence similarity with SEQ ID NO: 1 in its 16S rRNA gene and a *L. plantarum* strain having at least 97% sequence similarity with SEQ ID NO: 4 in its 16S rRNA gene.

10. The method of claim 9, wherein the *L. pentosus* strain is *L. pentosus* YUN-V1.0 deposited under accession number LMG P-29455 and *L. plantarum* YUN V2.0 deposited under accession number LMG P-29456.

11. The method of claim 9, wherein the *L. plantarum* strain is *L. plantarum* YUN V2.0 deposited under accession number LMG P-29456.

12. The method of claim 9, wherein the probiotherapy comprises restoring or maintaining a healthy female microbiota in the subject.

13. The composition of claim 4, wherein the *Lactobacillus* strain is anhydrous.

* * * * *